United States Patent [19]

Hasselbach et al.

[11] Patent Number: 5,049,283

[45] Date of Patent: Sep. 17, 1991

[54] METHOD FOR THE RECOVERY OF AQUEOUS SOLUTIONS OF FREE, NEUTRAL α-AMINO ACIDS FROM AQUEOUS SOLUTIONS OF THEIR ALKALI-METAL SALTS

[75] Inventors: Hans-Joachim Hasselbach, Hanau; Axel Kleeman, Mühlheim; Herbert Klenk, Hanau; Horst Weigel, Rodenbach, all of Fed. Rep. of Germany

[73] Assignee: Degussa Aktiengesellschaft, Fed. Rep. of Germany

[21] Appl. No.: 483,048

[22] Filed: Feb. 21, 1990

[30] Foreign Application Priority Data

Feb. 21, 1989 [DE] Fed. Rep. of Germany ....... 3905275

[51] Int. Cl.$^5$ ............................................. B01D 15/04
[52] U.S. Cl. ................................... 210/662; 210/676; 210/681
[58] Field of Search ............... 210/662, 670, 676, 681; 436/90

[56] References Cited

U.S. PATENT DOCUMENTS 3,879,287  4/1975  Porter ................................. 210/676
4,714,767  12/1987  Tanaka et al. ...................... 210/259

OTHER PUBLICATIONS

Greenstein and Winitz, *Chemistry of the Amino Acids*, Wiley, 1961, p. 1459ff.

*Primary Examiner*—Stanley Silverman
*Assistant Examiner*—Krisanne Shideler
*Attorney, Agent, or Firm*—Cushman, Darby & Cushman

[57] ABSTRACT

Aqueous solutions of free, neutral α-amino acids are recovered from aqueous solutions of their alkali-metal salts. Two equally large rectifying columns filled with a strongly acidic cation exchanger in the H$^+$ form are used, the discharge of the first column being connected to the head of the second column. The solution of the alkali-metal salt is at first delivered to the head of the first column, then the residual solution, reduced by the alkali-metal cations adsorbed in the exchanger, is displaced to the second column by means of the addition of water. A product-free forerun is first separated at the discharge of the second column and, when free α-amino acid begins to exit in the flow-off from the second column, the receiver is changed and the delivery of water to the head of the first column continues further until a mixed pH between 5 and 7 has been achieved in the receiver. Then, the previously first column is decoupled and regenerated, the previously second column, which is now the first column, is coupled to a freshly regenerated column as second column and the entire process is repeated as often as desired.

5 Claims, No Drawings

METHOD FOR THE RECOVERY OF AQUEOUS SOLUTIONS OF FREE, NEUTRAL α-AMINO ACIDS FROM AQUEOUS SOLUTIONS OF THEIR ALKALI-METAL SALTS

The present invention relates to a method for recovering aqueous solutions of free, neutral α-amino acids from aqueous solutions of their alkali-metal salts by means of a strongly acidic cation exchanger in the H+ form.

BACKGROUND OF THE INVENTION

Aqueous solutions of alkali-metal salts of neutral α-amino acids are produced, e.g., in the alkaline hydrolysis of the corresponding α-amino nitriles.

The recovery of free, neutral α-amino acids from aqueous solutions of their alkali-metal salts by means of a strongly acidic cation exchanger in the H+ form is known (cf. e.g. Greenstein and Winitz, Chemistry of the Amino Acids, Wiley, New York and London, 1961, p. 1459 ff.). In this process, the alkali-metal cations and the α-amino acids are bound to the ion exchanger. After the ion exchanger has been washed out with water, the α-amino acid is eluted with a dilute, aqueous solution of ammonia. The ammonia is expelled when the eluate is evaporated, and it can, if necessary, be recovered. The free α-amino acid can be isolated from the residue. However, this known method has several disadvantages: Since the alkali-metal cations and the α-amino acid are bound to the ion exchanger, its effective capacity for the bonding of the alkali-metal cations is, at best, only half-available. Ammonia is required as an additional auxiliary agent. And, finally, the eluates are strongly diluted in comparison to the initial solutions and considerable amounts of water must therefore be evaporated, especially in the case of readily water-soluble α-amino acids such as glycine, alanine or α-amino butyric acid.

SUMMARY OF THE INVENTION

In accordance with the present invention, two equally large rectifying columns are used, and the discharge from the first column is connected to the head of the second column. The initial solution of the alkali-metal salt is at first delivered to the head of the first column, then the residual solution, reduced by the alkali-metal cations adsorbed in the exchanger, is displaced to the second column by means of the addition of water. A product-free forerun is first separated at the discharge of the second column and, when free α-amino acid begins to exit in the flow-off from the second column, the receiver is changed. The delivery of water to the head of the first column continues further until a mixed pH between 5 and 7 has been achieved in the receiver. Then, the first column is decoupled and regenerated. The second column is now used as the first column. It is coupled to a freshly regenerated column as second column and the entire process is repeated as often as desired.

Water is preferably added after the replacement of the receiver to the head of the first column, until a mixed pH has been achieved in the receiver which corresponds to the isoelectric point of the particular α-amino acid.

The advantages of the method of the invention reside in the fact that no additional elution agent is required and that the product solutions are not diluted in comparison to the initial solutions; the solutions are concentrated. The loss of α-amino acid is distinctly below 5%, and amounts as a rule to at the most 2%.

In order to carry out the method of the invention in a practical manner, two equally large and equally dimensioned rectifying columns are connected in series in such a manner that the discharge of the first column A is connected to the head of the second column B.

All commercially available, strongly acidic ion exchange resins are suitable as cation exchangers, especially those based on polystyrene cross-linked with divinyl benzene and functionalized with HO₃S— groups.

At first, the solution of the alkali-metal salt and then water are added at the head of column A. It is advantageous if the equivalent ratio of alkali-metal cations to the α-amino acid in the solution of the alkali-metal salt is between 0.9 to 1.5:1, preferably between 1.1 to 1.3:1. It is also advantageous if the solution contains anions other than carboxylate ions of the α-amino acid and hydroxyl ions, such as carbonate ions, hydrogen carbonate ions, halogenide ions or sulfate ions, at most in amounts of 0.1 equivalent, relative to the α-amino acid content.

The concentration of the solution of the alkali-metal salt is not subject to any lower limit because the effect of the concentration becomes all the more pronounced, the more dilute the initial solution is. An upper limitation may arise because the solubility product of the particular α-amino acid should not be exceeded by the effect of the concentration.

During the addition of the solution of alkali-metal salt and the subsequent displacement with water, a product-free forerun runs off at first at the discharge of column B. At first in column A, then also in column B, α-amino acid is also bound at first along with the alkali-metal cations. As further initial solution is added, the α-amino acid is displaced by following alkali-metal cations. Consequently, the concentration of α-amino acid rises above that in the initial solution in the particular zone of the resin bed in which this displacement process is taking place. The front of the alkali-metal cations constantly pushes the zone of the elevated concentration of α-amino acid ahead of itself, at first through column A, then also through column B. Finally, free α-amino acid begins to exit in the runoff of column B. This can be recognized by a mist which forms in the receiver because the density of the runoff clearly rises. This stage can also be recognized by measuring conductivity, because the conductivity of the runoff also changes significantly.

The amount of initial solution and the amount of displacement water must be coordinated in such a manner with one another that two essential conditions are met. First, an α-amino acid solution with a pH between 5 and 7 should accumulate at the discharge of column B in such an amount that as complete as possible a utilization of the exchange capacity of a column is achieved. Second, column A should be freed at the same time of initial solution by the displacement water to such an extent that it can be regenerated immediately thereafter.

It is advantageous to use a vessel as product receiver which is equipped with a mixing device, in the simplest case an agitator, and with a device for measuring the pH. The end of the product fraction is indicated by the fact that a mixed pH between 5 and 7, preferably the pH corresponding to the isoelectric point of the particular α-amino acid, has been reached in the product receiver.

Column A is now completely charged with alkali-metal cations and also already washed out with water. It is decoupled from column B and regenerated in a known manner with a dilute mineral acid, washed free of acid with water and backwashed.

On the other hand, column B is still not completely charged with alkali-metal cations. It is therefore now used for a further cycle as the first column and coupled to regenerated column A as second column in such a manner that the discharge of the first column (B) is connected to the head of the second column (A).

In order to save the waiting time during the regenerating of column A, it is advantageous if more than two columns are used so that a freshly regenerated column is always available when a new second column is required. This makes it possible to carry out the method of the invention in a quasi-continuous manner.

When determining the amount to be added, a distinction must be made between the start-up phase, in which two freshly regenerated rectifying columns are available and the subsequent production cycles, in which only one freshly regenerated rectifying column and on partially charged rectifying column are used.

The amount of initial solution to be added in the start-up phase ($V_{start}$) can be approximately calculated for a given exchange system and a given initial solution in accordance with the equation $$V_{start} = (A \times V_H \times K : Me^+_{eff}) \quad (1)$$

wherein A has a value between 2.3 and 2.7, preferably 2.5. In this equation, $V_H$ signifies the volume of the resin bed in a rectifying column, K the effective capacity of the resin in mole alkali-metal cations per liter resin, $Me^+_{eff}$ the amount of alkali-metal ions to be effectively exchanged in order to achieve a mixed pH of 6 in the production fraction in mole alkali-metal cations per liter initial solution.

$V_H$ and K are determined on the resin in the $Na^+$ form, $V_H$ on resin covered with water and K by means of acidimetric titration. $Me^+_{eff}$ can be determined in a preliminary test by means of acidimetric titration.

In an analogous manner, the amount to be added in the subsequent production cycles can be approximately calculated in accordance with the equation $$cycl = (V_H \times K : Me^+_{eff}) \quad (2)$$

in which $V_{Zykl}$ signifies the volume to be added for the solution of the alkali-metal salt and K and $Me^+_{eff}$ have the meanings already described. That means that the amount to be added in the production cycles is measured in such a manner that the exchange capacity of a column is completely utilized.

The invention is illustrated in more detail by the following examples:

EXAMPLE 1

An exchange system consisting of two columns and with a strongly acidic ion exchanger in the $H^+$ form (Lewatit® SP 112 of the firm Bayer AG) was used. The volume of each of the two resin beds was 13 liters, measured on the resin in the $Na^+$ form covered with water. The ratio of cross section to height of the resin bed was 1:6 in each instance, the useful capacity of the resin 1.5 mole $Na^+$/liter.

At first, an initial solution of the following composition 1.3 moles/l glycine
0.1 mole/l iminodiacetic acid (byproduct)
1.7 moles/l $Na^+$ prepared by means of the hydrolysis of amino acetonitrile with sodium hydroxide solution in an amount of 30.5 liters and then 13.0 liters water were added at the head of the first column at a pump speed of 60 liters/hour. Meanwhile, 37.0 liters product-free forerun accumulated at first as the runoff of the second column. The receiver was now changed and a product fraction collected until a mixed pH of 6 was observed in the receiver. The volume of the product fraction was 6.5 liters.

Then, the first column was decoupled and subjected to regeneration. The previously second column was connected as the current first column to a freshly regenerated column as the second column. This terminated the start-up phase and the actual production cycles were able to begin.

At first, 12.2 liters of the above initial solution and then 13.0 liters of water were added at the head of the first column. Meanwhile, at first 18.7 liters product-free forerun accumulated at the runoff of the second column. Now the receiver was changed again and a product fraction collected until a mixed pH of 6 was adjusted in the receiver. The volume of the product fraction was 6.5 liters.

This terminated the first production cycle. It was repeated seven times in exactly the same manner. A total of 52.0 liters of product solution of the following composition:

2.40 moles/l glycine
0.18 mole/l iminodiacetic acid
0.18 mole/l $Na^+$ were obtained during the eight production cycles. This corresponds to a recovery rate for glycine of 98%.

EXAMPLE 2

A more highly concentrated initial solution with the following composition:

2.00 moles/l glycine
0.20 mole/l iminodiacetic acid
2.60 moles/l $Na^+$ was worked up in the same exchange system as in Example 1.

In the start-up phase, 24.4 liters of this solution and 13.0 liters water were added. In the first ensuing production cycle, 8.1 liters initial solution and 13.0 liters water were added. 14.35 liters product-free forerun and 6.75 liters product solution accumulated.

In a total of eight production cycles, 54.0 liters product solution with the following composition:

2.35 moles/l glycine
0.24 mole/l iminodiacetic acid
0.24 mole/l $Na^+$ were obtained, which corresponds once again to a recovery rate for glycine of 98%.

A comparison of Examples 1 and 2 shows that the effect of the concentrating is all the more considerable, the more dilute the initial solution is.

EXAMPLE 3

An exchange system consisting of two columns with the same resin as in Example 1 was used. The volume of each of the two resin beds was 0.5 liter, measured once again on the resin in the $Na^+$ form covered with water. The ratio of cross section to height of the resin bed was likewise 1:6 in each instance.

An initial solution with the following composition:
1.2 moles/l D,L-α-amino butyric acid
1.3 moles/l Na+
was worked up at a pump speed of 2 liters/hour.

In the start-up phase, 1,440 ml of this solution and 500 ml water were added. 1,515 ml product-free forerun and 425 ml product solution were obtained. In the first ensuing production cycle, 575 ml initial solution and 500 ml water were added. 650 l product-free forerun and 425 l product solution accumulated.

In a total of ten production cycles, 4.25 ml product solution with a content of 1.60 moles/liter D,L-α-amino butyric acid and under 0.1 mole/liter Na+ were obtained. The recovery rate for the D,L-α-amino butyric acid was 98%.

EXAMPLE 4

An initial solution with the following composition:
1.00 mole/liter D,L-alanine
1.10 moles/liter Na+
was worked up in the same exchange system as in Example 3.

In the start-up phase, 1,705 ml of this solution and 500 ml water were added. 1,730 ml product-free forerun and 475 ml product solution were obtained. In the first ensuing production cycle, 680 ml initial solution and 500 ml water were added. 705 ml product-free forerun and 475 ml product solution accumulated.

In a total of ten production cycles, 4.75 l product solution with a content of 1.40 moles/liter D,L-alanine and under 0.10 mole/liter Na+ were obtained. The recovery rate for the D,L-alanine was 98%.

What is claimed is:

1. In a process for recovering an aqueous solution of a free, neutral α-amino acid from an initial aqueous solution of its alkali-metal salt by means of a strongly acidic cation exchanger in the H+ form; the improvement in which no elution agent is needed and wherein two equally dimensioned ion-exchange columns are used, the discharge of the first column is connected to the head of the second column, the initial solution of the alkali-metal salt is at first delivered to the head of the first column, then solution remaining after adsorption of alkali-metal cations in the first column is displaced to the second column by means of the addition of water to the head of the first column, a product-free forerun is first separated at the discharge of the second column and, when free α-amino acid begins to exit from the second column, a receiver is changed and the delivery of water to the head of the first column continues further until an average pH of the mixed solution between 5 and 7 has been achieved in the receiver, the previously first column is decoupled and regenerated, the previously second column, which is now used as the first column, is coupled to a freshly regenerated column as second column and the process et forth above is repeated.

2. A process as set forth in claim 1 in which water is added to the head of the first column, after the replacement of the receiver, until an average pH of the mixed solution has been achieved in the receiver which corresponds to the isoelectric point of the α-amino acid which is being recovered.

3. A process as set forth in claim 1 in which the equivalent ratio of alkali-metal cations to the α-amino acid in the initial solution is between 0.9 to 1.5:1.

4. A process as set forth in claim 1 in which the equivalent ratio of alkali-metal cations to the α-amino acid in the initial solution is between 1.1 to 1.3:1.

5. A process as set forth in claim 1 in which the initial solution contains anions other than carboxylate ions of the αamino acid and hydroxyl ions, at most in amounts of 0.1 equivalents per mole α-amino acid, relative to the α-amino acid content.

* * * * *